US009545240B2

(12) United States Patent
Ninomiya et al.

(10) Patent No.: US 9,545,240 B2
(45) Date of Patent: Jan. 17, 2017

(54) PORTABLE ULTRASOUND SYSTEM

(75) Inventors: Atsushi Ninomiya, Tokyo (JP);
Kazuyuki Yanase, Tokyo (JP); Masaru Yokoyama, Tokyo (JP); Takashi Kashiwagi, Tokyo (JP); Taisuke Matsushita, Tokyo (JP)

(73) Assignee: HITACHI, LTD., Tokyo (JP)

( * ) Notice: Subject to any disclaimer, the term of this patent is extended or adjusted under 35 U.S.C. 154(b) by 131 days.

(21) Appl. No.: 14/007,719

(22) PCT Filed: Jan. 20, 2012

(86) PCT No.: PCT/JP2012/051270
§ 371 (c)(1),
(2), (4) Date: Sep. 26, 2013

(87) PCT Pub. No.: WO2012/132506
PCT Pub. Date: Oct. 4, 2012

(65) Prior Publication Data
US 2014/0024936 A1 Jan. 23, 2014

(30) Foreign Application Priority Data
Mar. 28, 2011 (JP) .................................. 2011-070522

(51) Int. Cl.
*A61B 8/00* (2006.01)

(52) U.S. Cl.
CPC ............ *A61B 8/4427* (2013.01); *A61B 8/4411* (2013.01); *A61B 8/462* (2013.01); *A61B 8/467* (2013.01)

(58) Field of Classification Search
CPC ...... G06F 1/162; G06F 1/1607; G06F 1/1666; G06F 1/1667; G06F 1/1662; A61B 8/4427; A61B 8/462
See application file for complete search history.

(56) References Cited

U.S. PATENT DOCUMENTS 5,268,817 A * 12/1993 Miyagawa et al. ...... 361/679.07

7,129,931 B2 * 10/2006 Pappas .......................... 345/168
(Continued)

FOREIGN PATENT DOCUMENTS

EP    2 554 122      2/2013
JP    04-205215      7/1992
(Continued)

OTHER PUBLICATIONS

JP Office Action for Japanese Application No. 2013-507213, issued on May 27, 2014.
(Continued)

*Primary Examiner* — Long V Le
*Assistant Examiner* — Bradley Impink
(74) *Attorney, Agent, or Firm* — Baker Botts L.L.P.

(57) ABSTRACT

The present invention provides a portable ultrasound system being superior in operability and design properties, and being allowed to take various storage postures fitting to the volume of a storage place. The keyboard unit 50 provided with an input device such as a keyboard and the display unit 80 incorporating a display part are mounted on the main body unit 30 that incorporates a main part of the ultrasound diagnostic system, respectively about the rotation axes P1 and P2, independently, in such a manner as rotatable, and further the rotation axes P1 and P2 are on a common axis P. The rotation axis part 200 supporting the display unit 80 is supported by the bearing of the main body unit in a part lower than the axis P, allowing the display unit to be rotatable about the rotation axis Q that is orthogonal to the axis P. With this configuration, it is possible to take an operating posture that allows the display unit 80 being upright to swivel, and multiple storage postures in which the posture of the main body unit 50 with respect to the keyboard unit 50 and the display unit 80 are variously changed.

12 Claims, 7 Drawing Sheets

(56) References Cited

U.S. PATENT DOCUMENTS

| | | |
|---|---|---|
| 8,348,845 B2 | 1/2013 | Ninomiya et al. |
| 2007/0078346 A1* | 4/2007 | Park et al. .................... 600/459 |
| 2008/0249406 A1 | 10/2008 | Naruse |
| 2010/0056913 A1 | 3/2010 | Hirakui et al. |
| 2010/0305444 A1* | 12/2010 | Fujii et al. .................... 600/443 |

FOREIGN PATENT DOCUMENTS

| | | |
|---|---|---|
| JP | 05-053685 * | 5/1993 |
| JP | 8-252250 A | 10/1996 |
| JP | 2002-215267 | 7/2002 |
| JP | 2004-295758 | 10/2004 |
| JP | 2004-326440 | 11/2004 |
| JP | 2008-126015 A | 6/2008 |
| JP | 2008-253596 A | 10/2008 |
| JP | 2009-153917 A | 7/2009 |
| JP | 2010-57674 A | 3/2010 |
| JP | 2010-162107 A | 7/2010 |

OTHER PUBLICATIONS

EP Search Report for European Application No. 12764339.3, issued on Aug. 19, 2014.

* cited by examiner

PORTABLE ULTRASOUND SYSTEM

TECHNICAL FIELD

The present invention relates to a portable ultrasound system, and more particularly, it relates to a portable ultrasound system superior in convenience upon installation (installability).

BACKGROUND ART

As a conventional ultrasound diagnostic system, a wagon-type system provided with a movable wagon on which various equipment is mounted is the mainstream. Currently, however, a portable ultrasound system superior in portability is coming into a market. By way of example, a portable ultrasound system referred to as a notebook type is provided with a structure allowing a cover-like case incorporating a display device to be folded onto a thin main body unit (Patent Document 1, Patent Document 2, etc.) A portable ultrasound system referred to as a vertical type, is provided with a display device on the front surface of a main body unit being small in thickness, and a foldable keyboard is provided on the surface of the main body unit below the display device. With this configuration, in the state of using, input operation is performed by extending the keyboard in front of the display device, whereas in the state of nonuse, the keyboard is folded in such a manner as covering the display device. It is also suggested that the display device of this vertical type system is provided with a tilt mechanism so as to enhance visibility of the display device, and this allows the vertical angle to be changeable (Patent Document 3).

PRIOR ART DOCUMENT

Patent Document

Patent Document 1
Japanese Unexamined Patent Application Publication No. 2010-57674
Patent Document 2
Japanese Unexamined Patent Application Publication No. 2010-162107
Patent Document 3
Japanese Unexamined Patent Application Publication No. 8-252250

DISCLOSURE OF THE INVENTION

Problem to be Solved by the Invention

In the vertical ultrasound diagnostic system, the main body unit is vertical, and thus an area required for installation is small. Therefore, there is an advantage that when it is stored for nonuse, a keyboard is folded, allowing a wide use of table top. The ultrasound diagnostic system is, however, sometimes required to show a diagnostic image to a patient being examined, and it is necessary that the display device has a swivel function. The vertical type has a structure that the main body unit is equipped with the display device and the keyboard, and there is a problem that it is not easy to have the swivel function.

On the other hand, the Patent Document 2 suggests an ultrasound diagnostic system being a notebook type in which an arm supports a display device in such a manner that the display device is foldable into the main body, as well as the display device is coupled to the arm in such a manner as rotatable about the arm, thereby enhancing usability of an operator. However, in this system, in order to place the display device at the position allowing an operating panel to be operable, where a keyboard and the like are arranged, it is necessary to turn the relatively large display device by 180 degrees, and subsequently the arm is also turned. Therefore, improvement of operability is desired. Typically in the usage state, the notebook type system is used with putting the largest plane of the main body unit on the table top, and therefore, a large installation area is necessary both in the operating state and the installed state (stored condition).

In other words, any of the conventional portable ultrasound systems can be used with placing the keyboard in front of the display device in the usage state, but there are problems in operability or installability.

In view of the situation above, an object of the present invention is to provide a small-sized ultrasound diagnostic system being able to take various storage postures, with favorable usability.

Means to Solve the Problem

In order to solve the problems above, in the portable ultrasound system of the present invention, a keyboard unit provided with an input device such as a keyboard and a display unit incorporating a display device are independently mounted in such a manner as rotatable with respect to a main body unit that incorporates major parts of the ultrasound diagnostic system, and the axes of rotation of respective units are placed on a common axis, and the display unit is set to be rotatable about an axis that is perpendicular to the axis of rotation.

Effect of the Invention

According to the portable ultrasound system of the present invention, it is configured such that the keyboard unit and the display unit are independently supported in rotatable manner on the main body unit. This configuration allows various postures, such as an operating posture in which the display unit is made upright in the state where the main body unit and the keyboard unit are in substantially horizontal positions, a vertical storage posture (a first storage posture) in which the keyboard unit and the display unit are substantially vertical with respect to the main body unit, and a flat-type storage posture (a second storage posture) in which the keyboard unit and the display unit are substantially parallel to the main body unit.

BRIEF DESCRIPTION OF DRAWINGS

FIG. 1(a) to FIG. 1(c) illustrate external views of various postures;

FIG. 3(a) is an exploded perspective view showing a joint between the main body unit and the keyboard unit, and FIG. 3(b) illustrates a cross section of the front center of the main body unit;

FIG. 4(a) is a side view of the first storage posture, and FIG. 4(b) is a side view of the second storage posture;

FIG. 5(a) is a perspective view of the accessory adapter mount, FIG. 5(b) and FIG. 5(c) are respectively a plan view and a side view of the accessory adapter mount on which an ultrasound probe is placed;

FIG. 6(a) and FIG. 6(b) respectively illustrate cross sections of the front center of the main body unit when the display unit is in the different postures, and FIG. 6(c) is a perspective view showing the adapter mount formed on the second rotation axis;

BEST MODE FOR CARRYING OUT THE INVENTION

Figure 1:
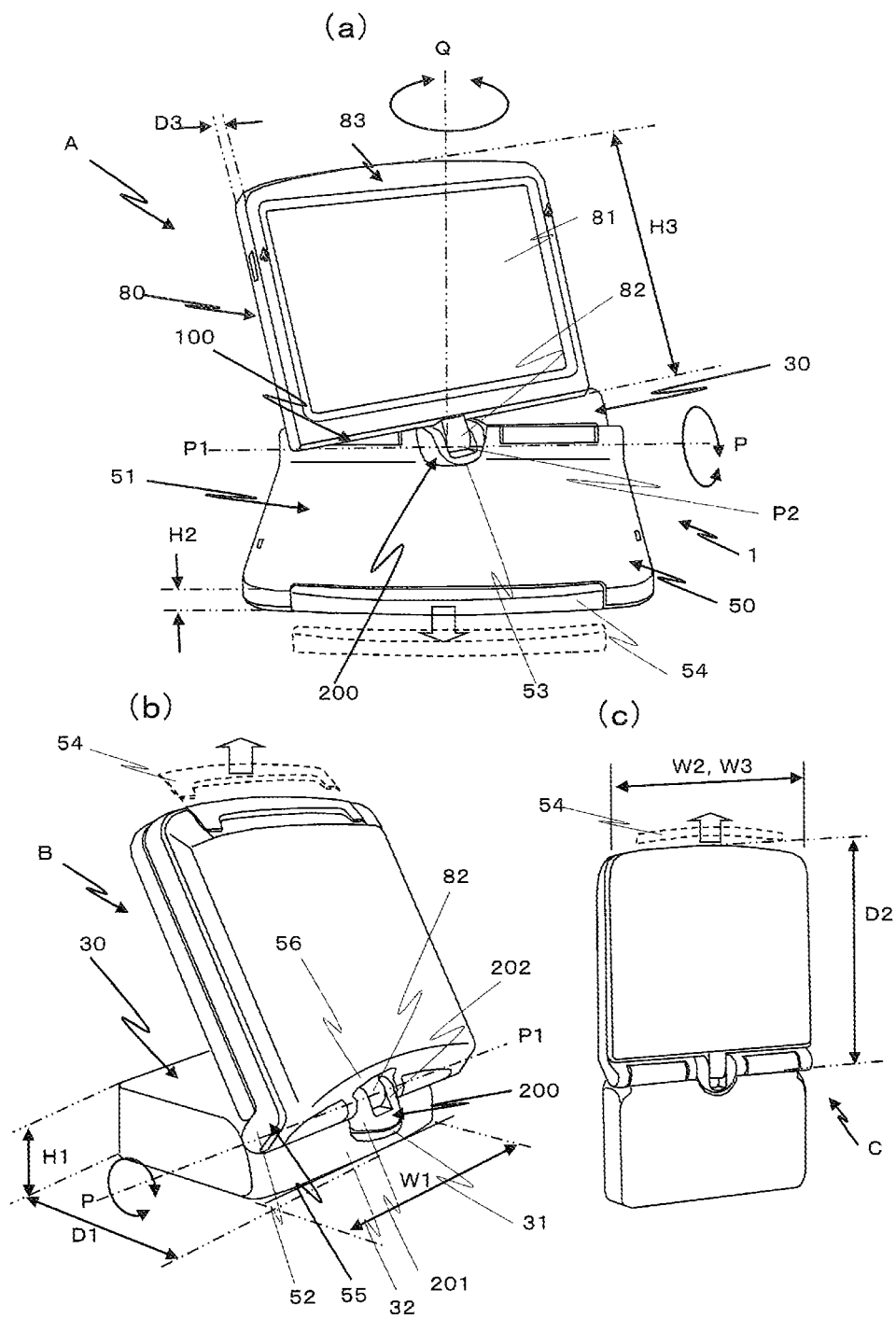
FIG. 1 illustrates one embodiment of the ultrasound diagnostic system according to the present invention as external perspective views.

The portable ultrasound system of the present invention is provided with a main body unit (30) incorporating an ultrasound measuring part, a display unit (80) coupled to the main body unit (30), having a display part for displaying an image generated by the ultrasound measuring part, and a keyboard unit (50) coupled to the main body unit (30), having an input device for inputting information necessary for the ultrasound measuring part. The portable ultrasound system is further provided with a first rotation axis part (100) axially supporting the keyboard unit (50) in rotatable manner about the first axis (P1) with respect to the main body unit (30), and a second rotation axis part (200) axially supporting the display unit (80) in rotatable manner with respect to the main body unit (3), about the second axis (P2) being on the same axis as the first axis but independent thereof, and a bearing part (202) for supporting the second rotation axis part (200) in rotatable manner about the third axis (Q) being perpendicular to the second axis.

According to the portable ultrasound system of the present invention, the rotation axis (the first rotation axis) (P1) of the keyboard unit with respect to the main body unit, and the rotation axis (the second rotation axis) (P2) of the display unit with respect to the main body unit are on the same axis. Therefore, it is possible to rotate, with respect to the main body unit, the keyboard unit and the display unit in a state of integrated, for example, being in a locked state, and thus much safer structure can be provided against external force, upon rotating each unit.

In a preferred embodiment of the portable ultrasound system according to the present invention, a bearing surface of the bearing part (202) is located in a lower part of the second axis (P2), when a part on the main body unit side is assumed as the lower part and a part on the display unit side is assumed as an upper part, placing the second axis (P2) therebetween.

According to the portable ultrasound system of the present invention, the rotation axis (a third rotation axis) (Q) for swiveling the display unit is set to be orthogonal to the rotation axis (the second rotation axis) (P2) about which the display unit (80) rotates with respect to the main body unit (30), thereby achieving the swiveling function by a compact device. In particular, the bearing part (202) for swiveling is provided closer to the main body side, than the second rotation axis, thereby locating a robust mechanism at a position less conspicuous in appearance and achieving both strengthening of the mechanism and design enhancement thereof.

In addition, in another preferred aspect of the portable ultrasound system according to the present invention, the keyboard unit (50) has a placement surface where the input device is arranged, and a bent part (55) that is bent with respect to the placement surface, and on this bent part, an arm part constituting the first rotation axis part (100) is formed.

The bent part (55) is provided on the keyboard unit (50), and the first rotation axis part (100) for rotating the keyboard unit is provided on this bent part, thereby allowing the first storage posture and the second storage posture to maintain parallelism between the keyboard unit and the display unit, and further improving safety against external force and enhancing the design thereof.

Other features of the present invention and effects thereof will be explained along with the following embodiments.

Hereinafter, an embodiment of the ultrasound diagnostic system according to the present invention will be explained with reference to the accompanying drawings. In the drawings attached to the present specification, the same elements are represented by the same symbols and tedious explanations will not be made.

Figure 2:
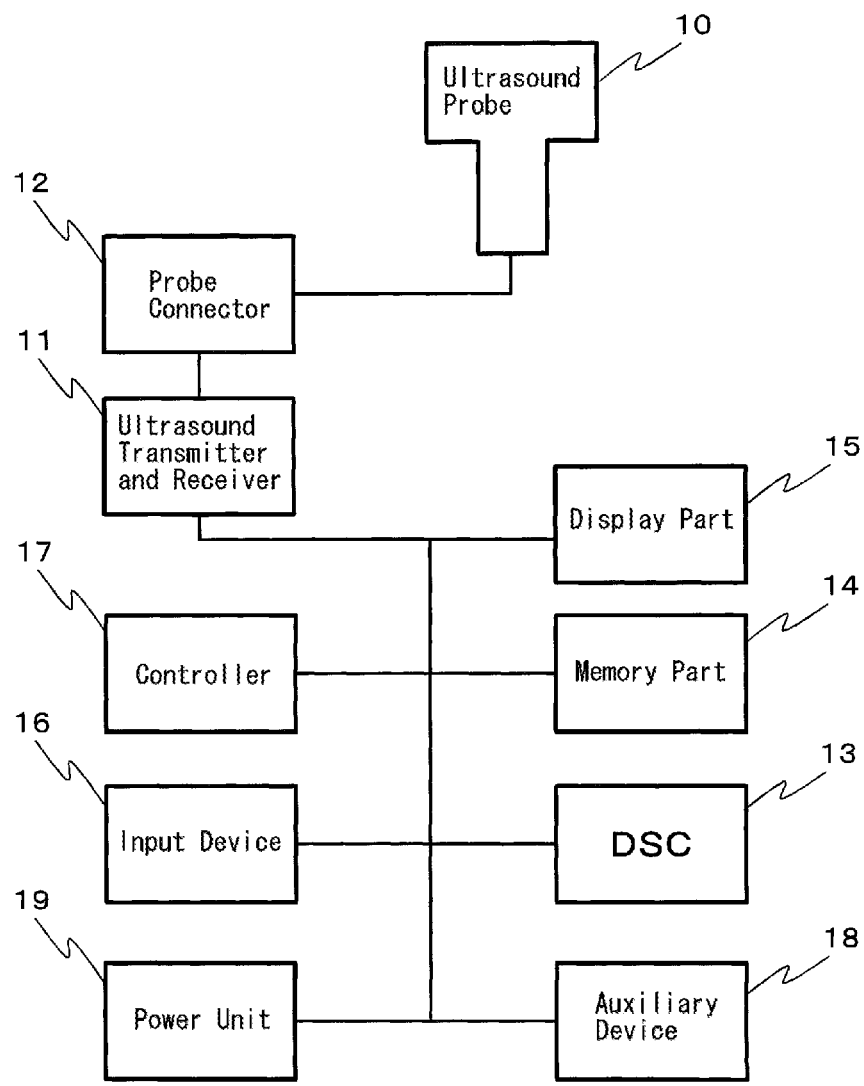
FIG. 2 is a block diagram illustrating one embodiment of a configuration of the ultrasound diagnostic system according to the present invention.

FIG. 1 illustrates one embodiment of the ultrasound diagnostic system according to the present invention as external views; FIG. 1(a) illustrates a usage state (operating posture A), FIG. 1(b) illustrates a vertical storage state (first storage posture B), and FIG. 1(c) illustrates a carrying state or a flat storage state (the second storage posture C). FIG. 2 is a block diagram illustrating a general configuration of the ultrasound diagnostic system.

The portable ultrasound system 1 as shown in FIG. 1 is provided with, as a primary structure, a main body unit 30 incorporating a device having main functions of this ultrasound diagnostic system, a keyboard unit 50 having an input operation key section not illustrated, and a display unit 80.

The configuration of the portable ultrasound system according to the present invention is the same as the configuration of a typical ultrasound diagnostic system, and as shown in FIG. 2, an ultrasound probe 10 having a group of ultrasound transducers, an ultrasound transmitter and receiver 11 for supplying a high-pressure pulse to this ultrasound probe 10, a probe connector 12 for connecting this ultrasound transmitter and receiver 11 with the ultrasound probe 10, a digital scan converter (hereinafter, referred to as "DSC") 13 for converting an echo into a digital signal, a memory part 14 made up of an image memory, a common-use graphics memory, an operator-use graphics memory, and the like, a display part 15 for displaying an ultrasound image, a GUI, and the like, an input device 16 having a track ball, a keyboard part, and the like, a controller 17 for integrally controlling this portable ultrasound system 1, an auxiliary device 18 such as an ECG measuring device, being connected as necessary, and a power unit 19 for supplying power to each part. Since the configuration and function of each part are the same as those publicly known, they are not explained here.

In the portable ultrasound system of FIG. 1, among those constitutional elements, the main body unit 30 incorporates mainly the functions of the ultrasound transmitter and receiver 11, the DSC 13, the controller 17, and the power unit 19, the display unit 80 is provided with the function of the display part 15, and the keyboard unit 50 is provided with the function of the input device 16. The main body unit 30 is further provided with connection terminals for connecting the probe connector 12 to establish connection with the ultrasound probe 10, and the auxiliary device 18. The ultrasound transmitter and receiver circuit, DSC, controller, and power unit being incorporated in the main body unit 30 are connected to the input device 16 provided in the keyboard unit 50 and to the display part 15 provided in the display unit 80, via cables not illustrated. Various ultrasound probes may be prepared as the ultrasound probe 10, and an ultrasound probe 10 suitable for measuring purpose is selected therefrom, and it is connected to the probe connector 12 to use the probe.

The portable ultrasound system of the present invention has features in the structure that the main body unit 30, the keyboard unit 50, and the display unit 80 are independent of one another, and the ends of the respective units are linked together, in such a manner as allowing rotating of the keyboard unit 50 and the display unit 80, and swiveling of the display unit 80. Specifically, with respect to the main body unit 30, the keyboard unit 50 and the display unit 80 are respectively supported in rotatable manner about the rotation axes P1 and P2 being independent of each other on the same axis P, and the display unit 80 is supported in swiveling manner about the rotation axis Q being orthogonal to the axis P. This structure allows, for example, to take various postures such as the operating posture A as shown in FIG. 1(*a*), the vertical storage posture B (the second storage posture) as shown in FIG. 1(*b*), the flat storage posture C as shown in FIG. 1(*c*) (the second storage posture).

Hereinafter, each part will be explained in detail. Firstly, an explanation will be made as to the three units, being major parts of the portable ultrasound system.

As shown in FIG. 1(*b*), the main body unit 30 has a substantially rectangular shape, being a flat shape; the depth D1 is longer than the height H1, and the width W1 is longer than the depth D1. In the operating posture A and the first storage posture, a plane determined by the depth and the width is placed on the installation surface. In the second storage posture, a slender plane determined by the height and the width is placed on the installation surface. Therefore, upon housing, it is possible to take either the first storage posture or the second storage posture, depending on the installation area and its volume. The keyboard unit 50 and the display unit 80 are mounted on one end 32 in the depth direction of the main body unit 30, each being rotatable with respect to the main body unit 30. In the operating posture A as shown in FIG. 1(*a*), this one end corresponds to the side facing to the operator, and it is referred to as a "front surface".

The front surface has a shape inclining rearward from the lower end to the upper end, and the first rotation axis part 100 for axially supporting the keyboard unit 50 is provided in proximity to the upper end of the front surface. At the center of the horizontal direction of the front surface of the main body unit 30, a rotation axis base part 31 extending forwardly is provided, and the second rotation axis part 200 is placed on the upper surface of this rotation axis base part 31. In the present embodiment, the rotation axis base part 31 extends out in arc-like manner upon viewed from the upper side, and this extended part is configured to be the size that is accommodated in the projected area of the second rotation axis part 200. The structures of the first rotation axis part 100 and the second rotation axis part 200 will be described later.

The keyboard unit 50 has a flat shape with the width W2 approximately the same as the width dimension W1 of the main body unit 30, the depth dimension D2 being larger than the depth dimension D1 of the main body unit 30, and relatively low height H2.

The keyboard unit 50 is provided with an input operation key layout 51 on the surface facing to the display unit 80 in the storage posture, the input operation key layout being equipped with input operation keys, not illustrated, such as a trackball and a keyboard part allowing character inputting. On one end of the depth direction of the input operation key layout 51, there is formed a bent part 55 that is bent obliquely toward the input operation key layout 51 side, and a first arm part 52 constituting the first rotation axis part 100 is formed on this bent part 55. The first rotation axis part 100 enables the keyboard unit 50 to turn about the rotation axis P1, allowing the keyboard unit 50 to move from the first storage posture substantially vertical as shown in FIG. 1(*b*) to the operating posture being horizontal as shown in FIG. 1(*a*), for instance.

A handle part 54 is provided on the other end in the depth direction of the keyboard unit 50, in other words, the end on the side opposite to the side where the bent part 55 is formed. As indicated by the bold arrow in FIG. 1, the handle part 54 is installed in slidable manner in the depth direction of the keyboard unit 50, and when the handle part 54 is not used, it is housed within the outer frame of the keyboard unit 50, thereby establishing an appearance being integrated with the keyboard unit 50. In the storage postures B and C as shown in FIG. 1(*b*) and FIG. 1(*c*), the handle part 54 is able to be drawn from the keyboard unit 50 and used as a handle, upon carrying the ultrasound diagnostic system of the present embodiment. In the operating posture as shown in FIG. 1(*a*), the handle part 54 may be drawn forwardly from the keyboard unit 50 to serve as a palm rest upon operating the keyboard part or the trackball, not illustrated, being arranged on the input operation key layout 51.

The display unit 80 has a shape of flat appearance similar to the keyboard unit 50, the width dimension W3 being approximately the same as those of the main body unit 30 and the keyboard unit 50, and the depth dimension (the height dimension H3 in the operating posture of FIG. 1(*a*)) is approximately the same as that of the input operation key layout 51 on the keyboard unit 50. The widths W1, W2, and W3, respectively of the three units 30, 50, and 80, are configured to be approximately the same size, thereby creating a sense of unity and continuity for the independent three units, and enhancing the design. In addition, the depth dimension D2 of the input operation key layout 51 on the keyboard unit 50 is made to substantially coincide with the height dimension H3 of the display unit 80, thereby achieving easy handling of both units in the storage postures and bringing about a sense of unity therebetween.

As for the display unit 80, a display screen part 81 such as an LCD is formed on the surface (display part installation surface) 83 that is facing to the keyboard unit 50 in the storage state as shown in FIG. 1(*b*) and FIG. 1(*c*), and on the lower end of the display unit, there is formed an arm part 82 constituting the second rotation axis part 200.

The second rotation axis part 200 enables the display unit 80 to turn about the rotation axis P2, and thus it allows moving from the substantially vertical posture as shown in FIG. 1(*a*) and FIG. 1(*b*) to the posture being parallel with the main body unit 30 as shown in FIG. 1(*c*). Since the rotation axis P2 of the second rotation axis part 200 is independent of the rotation axis P1 of the first rotation axis part 100, in the state where the storage posture is horizontal as shown in FIG. 1(*c*), the display unit 80 by itself is allowed to rotate with respect to the main body unit 30, thereby achieving the operating posture as shown in FIG. 1(*a*).

The second rotation axis part 200 includes a movable axis part 201 on which the bearing part 202 for accepting the arm part 82 is formed, and the movable axis part 201 is supported in such a manner as rotatable with respect to the main body unit 30, about the rotation axis Q that is orthogonal to the rotation axis P. With this configuration, the display unit 80 is allowed to swivel about the rotation axis Q in the operating posture A, where movement of the display unit 80 is not inhibited by the keyboard unit 50.

Figure 3:
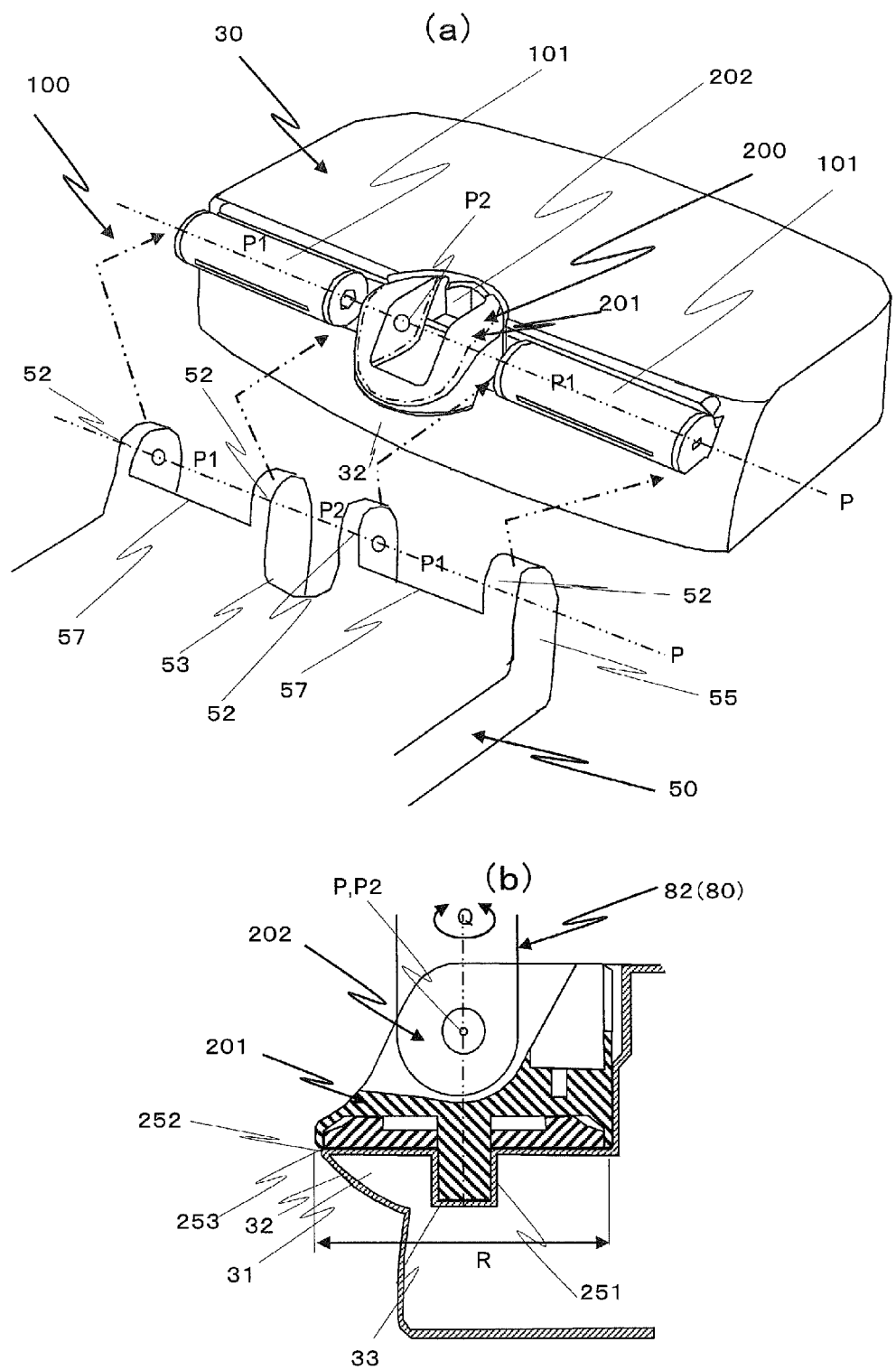
FIG. 3 illustrates an essential part of the ultrasound diagnostic system of FIG. 1.

Next, with reference to FIG. 3 and FIG. 4, the first rotation axis part 100 and the second rotation axis part 200 will be explained in detail. FIG. 3(*a*) is an exploded perspective view illustrating the joint between the main body unit 30 and the keyboard unit 50, and FIG. 3(*b*) is a cross sectional view illustrating the joint at the center of the front surface of the main body unit 30.

The first rotation axis part 100 is a significant structure for supporting the keyboard unit 50 in rotatable manner that is weighty relative to the main body unit 30, and for maintaining the first storage posture and the second storage posture as shown in FIG. 1(*b*) and FIG. 1(*c*), and therefore, the first rotation axis part is provided with a robust configuration. Specifically, as shown in FIG. 3(*a*), the first rotation axis part 100 is made up of a cylindrical fixed axis part 101 that is fixed on the main body unit 30, and the first arm part 52 formed on the bent part 55 of the keyboard unit 50.

In the embodiment being illustrated, a pair of fixed axis parts 101 on the left and right sides are provided in fixed manner on the front surface of the main body unit 30 in proximity to the upper end being inclined rearward. The second rotation axis part 200 is placed in the space at the center between the pair of the fixed axis parts 101 on the left and right sides. On the bent part 55 of the keyboard unit 50, there are formed notches 57 and 53, respectively on the two positions left and right in association with the pair of the fixed axis parts 101, and on the center position in association with the second rotation axis part 200. As remaining parts, there are formed two pairs of the first arm parts 52, respectively on the left and right, four in total. These first arm parts 52 are mounted in rotatable manner on both sides of each pair of the first axis parts 101, thereby forming the first rotation axis part 100 being robust in structure. With this structure, the rotation axis P1 is formed along the longitudinal direction of the cylindrical fixed axis part 101, and this allows the keyboard unit 50 to rotate about the rotation axis P1.

As illustrated in detail in the cross-sectional view of FIG. 3(*b*), the second rotation axis part 200 is mainly made up of the second arm part 82 formed on the lower end of the display unit 80, a movable axis part 201 coupled to the second arm part 82, and a rotation axis base part 31 formed on the front surface of the main body unit 30 and serving as the bearing of the movable axis part 201.

The second arm part 82 has a cross section of substantially U-shape on the surface being orthogonal to the display screen 81 of the display unit 80, the tip of the U-shape is coupled to the movable axis part 201, and the other end is fixed to the display unit 80. At the U-shaped tip, there is formed a hole at the position corresponding to the axis P2 that passes through the movable axis part 201, and the tip is supported on the movable axis part 201 in a rotatable manner about the rotation axis P2. When the display unit 80 takes the storage posture, the rotation axis P2 is on the axis P that is common to the rotation axis P1 of the first rotation axis part 100.

The movable axis part 201 is a member having a substantially cylindrical shape being low in height, made up of a circular upper surface and a bottom surface, and a side surface connecting those upper surface and bottom surface. On this upper surface, the bearing part 202 is formed for rotatably supporting the aforementioned arm part 82 of the display unit 80. The upper surface is inclined gently toward the front, and approaches the bottom surface. With this shape, it is possible to make the notch 53 relatively small, which is formed on the bent part 55 of the keyboard unit 50 in order to avoid interference with the movable axis part 201, thereby preventing degradation in design properties due to the notch 53.

The bearing part 202 formed on the upper surface of the movable axis part 201 has a rounded bottom, so as not to constitute an obstacle to the rotating action of the arm part 82 about the rotation axis P2. In addition, a distance in the left-right direction (the direction of the axis P2) between both side walls of the bearing part 202 is substantially equal to the width of the second arm part 82 in the direction of the rotation axis P2, and this configuration restricts the movement of the arm part 82 in the direction of the rotation axis P2. The second rotation axis part 200 made up of the movable axis part 201 and the second arm part 82 on the lower end of the display unit 80 enables turning (folding) of the display unit 80 about the rotation axis P2.

Figure 6:
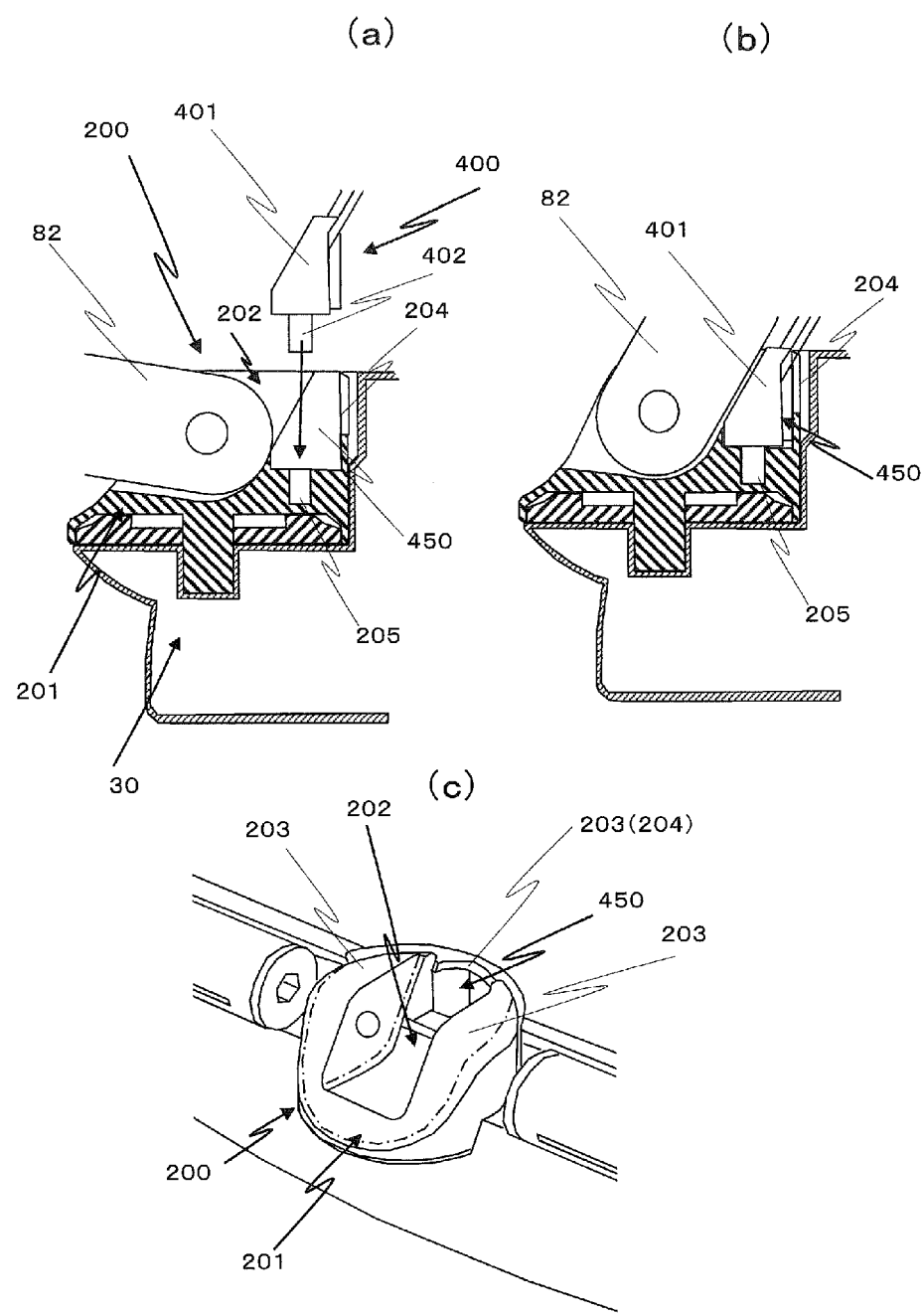
FIG. 6 illustrates the adapter mount in the ultrasound diagnostic system of FIG. 1.

In the embodiment as shown in FIG. 3(*b*), space other than the range of the movement of the second arm part in the bearing part 202 is used to provide space for an adapter for mounting accessories, and the like. This function will be described later. In this case, in order to prevent degradation of visibility of the display screen part 81 due to rearward toppling of the display unit 80 in the operating posture A, a structure as shown in FIG. 6(*c*) is employed, that is, the bearing part 202 which rotatably supports the tip of the second arm part 82 by both sides is provided with a rim 203 which surrounds the backside of the second arm part 82, so as to hold the second arm part 82 to prevent backward falling. In other words, the rim 203 is formed in such a manner that both sides and the backside are continuous, except the front side.

On the other hand, there is formed a swiveling axis 251 that extends downwardly allowing the swiveling of the display unit 80, on the bottom surface opposite to the surface where the bearing part 202 of the movable axis part 201 is formed, and a ring-like movable contact surface 252 is formed, constituting the swiveling plane R around the swiveling axis 251. The rotation axis Q of the swiveling axis 251 is orthogonal to the rotation axis P2 of the second rotation axis part 200. This configuration allows the display unit 80 to swivel about the rotation axis Q within a minimum range of movement, thereby configuring the overall device to be a compact size.

There is formed a concave portion (rotation axis base part 31) fitting to the shape of the aforementioned movable axis part 201, on the surface inclined rearward at the front center of the main body unit 30. This rotation axis base part 31 is provided with an upper surface having a shape that is included in the projected area of the movable axis part 201 being circular in shape. The upper surface of the rotation axis base part 31 is provided with a bearing part 33 for supporting the swiveling axis 251 of the movable axis part 201, and a fixed contact surface 253 formed around the bearing part 33 to support the ring-like movable contact surface 252. Here, the rear part of the fixed contact surface 253 is formed in such a manner as cutting into the front surface of the main body unit 30, the front surface being inclined rearward.

The aforementioned structure of the second rotation axis part 200 allows the display unit 80 to rotate about the rotation axis P2 with respect to the main body unit 30, independently of the keyboard unit 50, and also allows the display unit 80 to swivel about the axis Q in the operating posture A where the display unit 80 is set apart from the keyboard unit 50.

The present embodiment employs a structure that the rotation axis base part 31 is formed in such a manner as extending forwardly at the lower position between the pair of the fixed axis parts 101, in other words, at the lower position of the front center of the main body unit 30, and this rotation axis base part 31 supports the movable axis part 201. Therefore, it is possible to configure such that the rotation axis P2 of the display unit 80 coincides with the rotation axis P1 of the keyboard unit 50 on the rotation axis P.

It is to be noted that rotating about the axis P2 of the display unit 80 and swiveling about the axis Q may also be achieved, by fixing the movable axis part 201 onto the main body unit 30 and providing a swiveling axis on the arm part 82 side of the display unit 80 that is axially supported. In that case, however, a large-sized structure of the rotation axis Q is placed at a higher position of the portable ultrasound system 1, so as to reserve a wide swiveling plane R, and this may degrade the design. Particularly in the present embodiment, where the rotation axis P2 of the display unit 80 is made to coincide with the rotation axis P1 of the keyboard unit 50, if a large-sized structure of the rotation axis Q is exposed in the upper part of the first rotation axis part 100 that allows the keyboard unit 50 to be rotatable, this may not only degrade the design properties, but also impair the rotation about the rotation axis P2. On the other hand, the present embodiment employs the structure that the rotation axis Q is provided in the lower part of the rotation axis P2, it is possible to solve the problems that the design may be degraded and rotation of the display unit 80 about the rotation axis P2 is hampered.

Next, an explanation will be made as to the shapes of the front of the main body unit 30 and the bent part 55 of the keyboard unit 50, being preferable for arranging the first rotation axis part 100 and the second rotation axis part 200 as described above.

As already stated, the front surface of the main body unit 30 is formed on the curved surface that is inclined rearward from the lower end toward the upper end, and that is bowed outwardly from both side edges towards the center. Since the first rotation axis part 100 is arranged in proximity to the upper edge inclined rearward, it is possible to achieve a compact placement of the first rotation axis part 100 being a robust structure, without expanding largely from the front surface.

The movable axis part 201 having a cylindrical shape constituting the second rotation axis part 200 is placed between the first rotation axis parts 100 being in pair respectively on the left and right, that is, at the center of the front surface, and the bearing part 33 of the movable axis part 201 is formed on the main body unit 30. As shown in FIG. 3(b), on the bottom of the bearing part 33, there is formed an extended part 32 that extends in arc-like manner toward the front in the depth direction of the main body unit 30, in such a manner as fitting to the bottom of the movable axis part 201.

The bottom 252 of the movable axis part 201 and the bottom 253 of the concave portion formed on the front surface of the main body unit 30 are brought into contact with each other, and constitute the swiveling plane R (the movable contact surface 252 and the fixed contact surface 253) for the swiveling motion of the movable axis part 201. Typically in the case of the swiveling mechanism, a large swiveling plane R is necessary for supporting the display unit 80 (the second arm part 82) stably and robustly around the rotation axis Q. In the present embodiment, the movable contact surface and the fixed contact surface are shaped in such a manner as extending from the front side of the main body unit 80, thereby reserving a large swiveling plane R and ensuring stable swiveling movement of the display unit 80.

There is formed an indentation 56 (FIG. 1(b)) on the backside surface (opposite surface of the input operation key layout 51, in proximity to the bent part 55 of the keyboard unit 50 that rotates with respect to the main body unit 30, in such a manner as fitting to the arc-like extended part 32 on the front surface of the aforementioned main body unit 30. With this indentation 56, though the size of the notch 53 for the second rotation axis part 200, being formed on the bent part 55, is restricted to be relatively small, it is possible to avoid collision between the bent part 55 and the extended part 32 on the front surface of the main body unit 30, when the keyboard unit 50 is rotated about the rotation axis P1.

Figure 4:
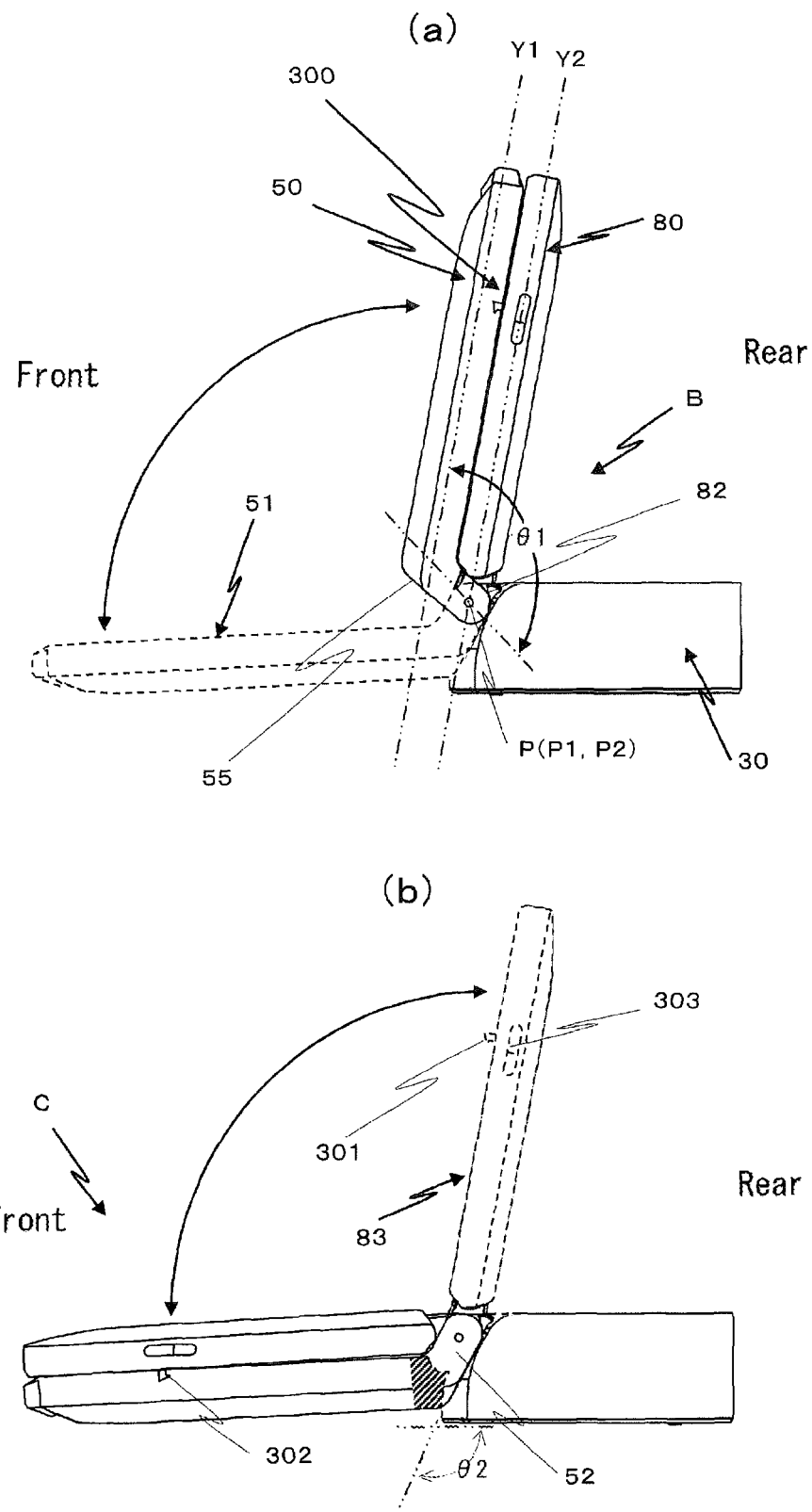
FIG. 4 illustrates functions of the ultrasound diagnostic system of FIG. 1.

With reference to FIG. 4, a structure of the bent part 55 will be explained in detail. FIG. 4(a) is a side view illustrating the first storage posture of the portable ultrasound system according to the present embodiment, corresponding to FIG. 1(b), and the dotted line indicates the operating posture A in which only the keyboard unit 50 is open. FIG. 4(b) illustrates the state where the display unit 80 in the operating posture (indicated by the dotted line) is closed, showing the second storage posture C of FIG. 1(c).

As already explained, in the present embodiment, the keyboard unit 50 and the display unit 80 rotate about the rotation axes P1 and P2, respectively, being on the common axis P. Here, if both are shaped linearly from one end supported by the rotation axis to the other end on the opposite side, the keyboard unit 50 may form a predetermined angle with the display unit 80, being defined by a thickness or the like at one end. In other words, they cannot be parallel to each other. On the other hand, in the present embodiment, one end of the keyboard unit 50 is formed as the bent part 55, and on this bent part 55, the arm part 52 constituting the first rotation axis part 100 is formed, thereby allowing the display unit 80 to be placed into the space made up of two planes that are defined by the bent part 55 and the input operation key layout 51 of the keyboard unit 50. Consequently, in the storage state as shown in FIG. 4, it is possible to keep the primary planes Y1 and Y2 of both substantially parallel with each other, allowing a lock mechanism to be provided easily for locking the coupled state therebetween, and in the storage posture, the input operation key layout 51 and the display screen 81 facing to each other may be protected against external forces.

When only the keyboard unit 50 is rotated about the rotation axis P1, to be brought into the operating posture A indicated by the dotted line in FIG. 4(a), or in the second storage state C as shown in FIG. 4(b), this bent part 55 abuts against the front surface of the main body unit 30, and thereby stabilizing the posture of the keyboard unit 50 under any of those conditions.

The angle θ1 of the bent part 55 of the keyboard unit 50 with respect to the primary plane Y1 is not limited, but in the embodiment being illustrated, the angle is set to be 90 degrees or larger, to fit to the inclination of the front surface of the main body unit 30. This configuration allows to take the operating posture A (FIG. 1(a)) or the second storage posture C (FIG. 1(c)) in which the keyboard unit 50 is substantially horizontal or the front side thereof is lowered, and the first storage posture B (FIG. 1(b)) in which the upper end is inclined rearward a little. Further in the present embodiment, the indentation 56 is formed on the lower end of the keyboard unit 50 in the first storage posture as shown in FIG. 1(b), configuring a rounded shape, thereby achieving a preferable design.

If the angle of bend θ1 is too large, the input operation key layout 51 may become narrower, or it is necessary to set the depth dimension D2 of the keyboard unit 50 to be a larger value. On the other hand, in the present embodiment, when the front portion of the upper surface of the main body unit 30 is viewed from the top, it has an arc-like shape; the center extended forwardly and the outline receding gradually as approaching both sides, the inclination angle θ2 on both sides is smaller than the rearward inclination angle at the center. In addition, each angle of bend θ1 of the bent parts 55 on both ends of the keyboard unit 50 is formed to conform to the inclination angle θ2 on both sides of the front surface of the main body unit 30. The indentation 56 is formed at the center part of the bent part 55, having the inclination angle being larger relative to both ends, in order to avoid the extended part 32 on the front surface of the main body unit 30. With the structure as described above, an appropriate angle is given to the bent part 55 without enlarging the depth dimension D2 of the keyboard unit 50, thereby enhancing the design of the front surface of the main body unit 30 in the first storage posture as shown in FIG. 1(b).

A basic structure of the portable ultrasound system according to the present embodiment has been explained. Here, it is to be noted that the portable ultrasound system of the present embodiment may be further provided with various additional mechanisms, on the basis of the rotating and swiveling structures and the configuration of each of the aforementioned units 30, 50, and 80. Hereinafter, the examples thereof will be explained.

Firstly, with reference to FIG. 4, a lock mechanism between the keyboard unit 50 and the display unit 80 will be explained.

The lock mechanism is provided to maintain the state where the keyboard unit 50 and the display unit 80 are closed. In the embodiment as illustrated, the lock mechanism 300 is made up of an opening for locking 302 provided on the input operation key layout 51 of the keyboard unit 50, a hook part 301 provided on the display part installation surface 83 of the display unit 80, and a release button 303 for releasing the locked state.

The hook part 301 and the release button 303 are linked via a link mechanism provided with a spring not illustrated, and those elements are linked in such a manner that the tip of the hook part 301 is moved by manipulating the release button 303. When the keyboard unit 50 and the display unit 80 are closed, the hook part 301 is inserted into the opening for locking 302 in the keyboard unit 50, and with a subtle turning against the urging force of the spring, the hook part is further inserted into the opening 302, until the keyboard unit 50 and the display unit 80 come into the state completely closed. Under this condition, with the urging force of the spring, the hook part is brought into the condition that it is hooked on the edge of the opening 302, thereby locking the link between the keyboard unit 50 and the display unit 80. On the other hand, the release button 303 is manipulated to move the hook part 301 a little, from the engaged position on the edge of the opening for locking 302, toward the opening part, thereby releasing the locked state between the hook part 301 and the opening for locking 302, and as shown in FIG. 4(a), the keyboard unit 50 is allowed to rotate about the axis P1 by itself.

The keyboard unit 50 and the display unit 80 are rotated about the axis P commonly used. Therefore, they are allowed to rotate about the axis P, with respect to the main body unit 30, in the state that both are locked. Conversely, the main body unit 30 is allowed to rotate by itself about the axis P, with respect to the keyboard unit 50 and the display unit 80 being joined in the locked state, thereby changing the posture from the vertical storage state as shown in FIG. 1(b) to the flat storage state as shown in FIG. 1(c).

According to the present embodiment as described above, the keyboard unit 50 and the display unit 80 are supported respectively by different rotation axes, and those rotation axes P1 and P2 are placed on the same axis, thereby allowing the keyboard unit 50 and the display unit 80 to rotate in the locked state with respect to the main body unit 30, and an identical lock mechanism is sufficient for the different storage postures.

If a particular lock means or a means for restricting a range of rotation is not provided, the range of rotation of the keyboard unit 50 is from the position (the first storage posture in FIG. 4(a)) abutting against the display unit 80 under the condition that the display unit 80 is fixed on the back surface of the bearing part 202 of the second rotation axis part 200, to the position (indicated by the dotted line in FIG. 4(a)) where the bent part 55 of the keyboard unit 50 abuts against the front inclined part of the main body unit 30, after the rotation toward the device installation surface side. Here, it is further possible that the first rotation axis part 100 of the keyboard unit 50 is provided with a fixing means that is able to withstand the self-weight of the keyboard unit 50, the fixing means being already known as a means for fixing the rotation at a predetermined position or any optional position, or the first rotation axis part 100 may be provided with a lock means for completing fixing the rotation of the keyboard unit 50 in the first storage posture and in the second storage posture. With this kind of fixing means being provided for fixing the rotation, it is also possible to change the angle (inclination) of the display unit (display screen) 80 in the operating posture, with respect to the main body unit 30 or the keyboard unit 50. Upon the rotation of the keyboard unit 50 and the display unit 80 independently or in the state of being joined, this fixing means may inhibit abrupt rotation and mitigate the impact along with the rotation, thereby reducing the possibility of breakage. If there is provided a lock means for fixing the storage posture, it is not necessary to install the same type of fixing means in the second rotation axis part 200 that axially supports the display unit 80, thereby enabling the second rotation axis part 200 to be downsized. In addition, this allows easy carriage by the use of the handle part 54, while maintaining either of two storage postures as shown in FIG. 1.

As an additional function, an explanation will be made as to an attaching/detaching mechanism of the adapter for mounting accessories. In general, as for the ultrasound diagnostic system, there are needs for using more than one ultrasound probe 10, depending on the portion to be diagnosed. In the present embodiment, there is provided a mechanism for installing the adapter in detachable manner, in order to reserve a space for placing more than one ultrasound probe 10, without degrading portability being a feature of the portable type device.

Figure 5:
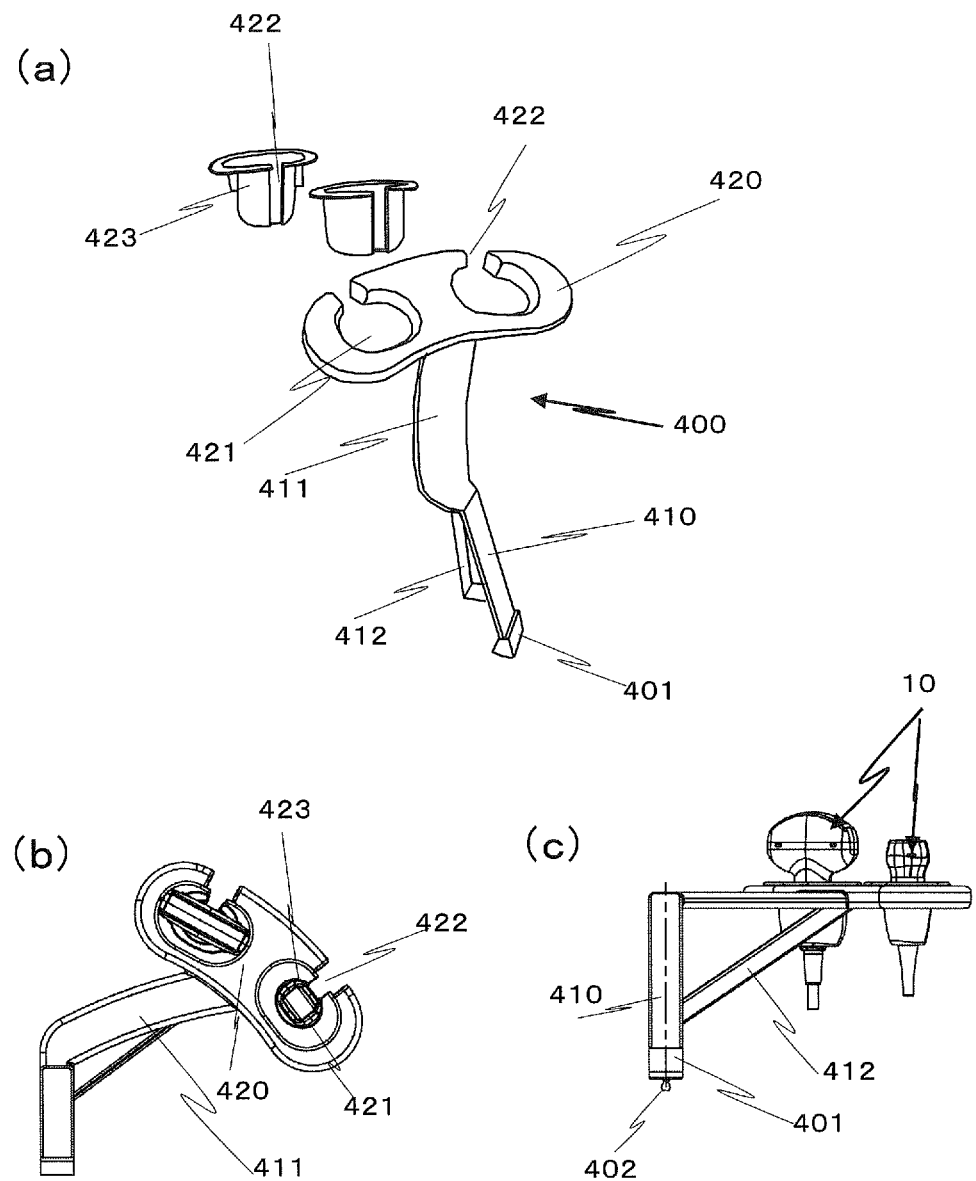
FIG. 5 illustrates an accessory adapter mount being installable on the ultrasound diagnostic system of FIG. 1.
Figure 7:
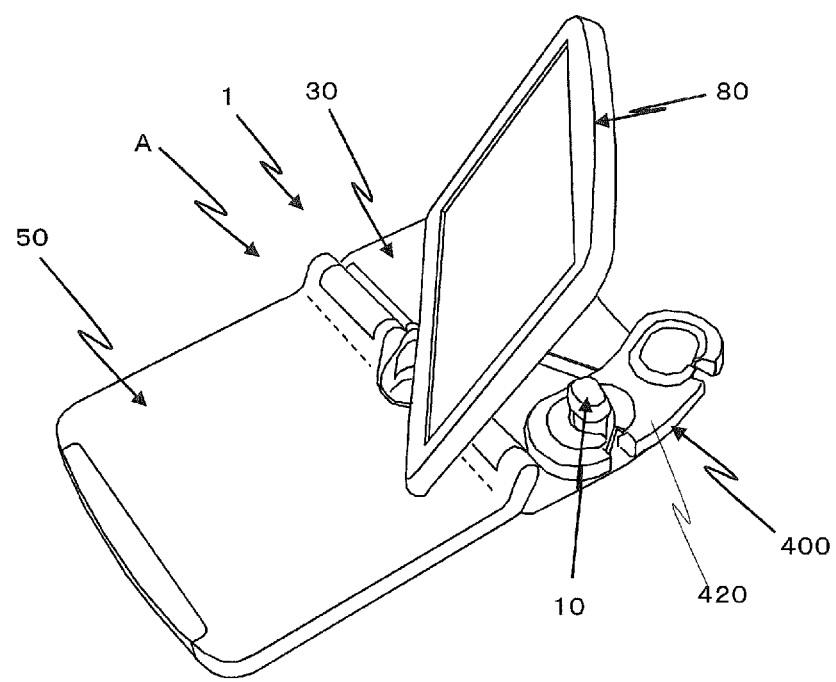
FIG. 7 is a perspective view illustrating the operating state when the accessory adapter as shown in FIG. 5 is installed on the ultrasound diagnostic system as shown in FIG. 1.

Figures from FIG. 5 to FIG. 7 illustrate an example of the mechanism for attaching/detaching the adapter. FIG. 5 illustrates a structure of the adapter for mounting accessories of the portable ultrasound system relating to the present embodiment, FIG. 5(a) is a perspective view of the adapter for mounting accessories, FIG. 5(b) and FIG. 5(c) are, respectively, a plan view and a front view of the adapter in the state where accessories are mounted. FIG. 6 illustrates a structure for installing the adapter for mounting accessories of the portable ultrasound system relating to the present embodiment; FIG. 6(a) illustrates installation of the adapter for mounting accessories, FIG. 6(b) is a vertical cross-sectional view of the movable axis part in the state where the adapter for mounting accessories is fixed, and FIG. 6(c) is a perspective view of the movable axis part. FIG. 7 is a perspective view of the portable ultrasound system in the state that the adapter for mounting accessories is installed.

Firstly, with reference to FIG. 5, a structure of the adapter for mounting accessories (hereinafter, simply referred to as "adapter") will be explained. As shown in FIG. 5(a), the adapter 400 is made up of a table top 420 having a deformed track shape with rounded circumference, a lateral supporter 411 for supporting the table top 420, extending in substantially the same direction as the plane direction of the table top 420, a primary supporter 410 coupled to the other end of the lateral supporter 411, an installation leg 401 provided on the lower end of the primary supporter 410, and a reinforcing supporter 412 linking the end of the lateral supporter 411 on the table top side, with the lower end of the primary supporter 410.

There are provided on the table top 420, multiple apertures 421 for placing the ultrasound probe 10, and the like. Those apertures 421 are notched in the outer peripheral direction, and the code of the ultrasound probe 10 is made to pass through the notch 422, thereby allowing the ultrasound probe 10 to be placed in the aperture 421. The aperture 421 of the table top 420 may be equipped with an aperture cover 423 made of a flexible resin material, in order to place the ultrasound probe 10 stably without any scratching. On this occasion, this aperture cover 423 has an appearance of C-shape, obtained by notching a ring-like shape, and this provides a structure enabling a code to pass through. FIG. 5(b) and FIG. 5(c) illustrate that two types of ultrasound probes 10 are put on this C-shaped cover 423.

In the present embodiment, a configuration for installing the adapter 400 with the aforementioned structure is provided on the second rotation axis part 200 for supporting the display unit 80. As already explained, the second rotation axis part 200 is provided with the movable axis part 201 that is supported at its lower part by the main body unit 30 in such a manner as allowing a swiveling motion, and the upper part of the movable axis part 201 is coupled to the display unit 80 (not illustrated) allowing a folding motion. On the upper surface of the movable axis part 201, there is formed a concave part (the bearing part 202) to accept the second arm part 82 of the display unit 80.

The second arm part 82 of the display unit 80 being coupled to the bearing part 202 of the movable axis part 201 may be moved as shown in FIG. 6(a), from the horizontal posture (the second storage posture C) in which the display installation surface 83 faces to the downside, to the posture (the operating posture A) as shown in FIG. 6(b) in which the display installation surface 83 is upright and looking forward. In this situation, a mount 450 is provided for installing the adapter in the space of the rear side of the bearing part 202 which determines the range of movement of the second arm part 82.

Specifically, as shown in FIG. 6(c), a concave-like mount 450 being notched forwardly is formed in the front section of the rearward rim 204 of the bearing part 202, and on the bottom of the mount 450, there is provided an fitting hole 205 into which the installation leg 401 of the adapter 400 is fitted. In order to fit to the shape of the mount 450, the installation leg 401 of the adapter 400 has a shape wider in the lower part and narrower in the upper part, and a projection 402 is provided on the bottom.

The adapter 400 is allowed to be installed easily on the concave-like mount 450 formed on the bearing part 202, according to the following procedure. Firstly, as shown in FIG. 6(a), the display unit 80 is tilted forward and the mount 450 is exposed. The installation leg 401 of the adapter 400 is inserted into the mount 450 being exposed, and the projection 402 on the bottom is fitted into the fitting hole 205 of the mount 450, thereby installing the adapter 400. Under this condition, the adapter 400 is held only unstably in the meantime. Next, as shown in FIG. 6(b), by resuming the posture in which the display unit 80 stands, the installation leg 401 is stably held between the rearward rim 204 and the second arm part 82.

With this structure, in the state of FIG. 6(b), the adapter 400 is fixedly supported in the rear of the display unit 80. In addition, since the adapter 400 is installed on the movable axis part 201 together with the display unit 80, as shown in FIG. 7, the adapter turns in an interlocked manner with the swivel of the display unit 80, and therefore there is no collision with the display unit 80. In addition, if the display unit 80 is tilted forward, it is possible to remove the adapter 400 easily.

It is to be noted that the adapter 400 relating to the present embodiment employs the table top 420 as the accessories holder, but the adapter is not limited to this shape. By way of example, a rod-like member available for hooking the code of the ultrasound probe 10, or any other shape having the same function is applicable.

According to the portable ultrasound system of the present embodiment, in the operating posture A, it is possible to easily place an accessory such as the ultrasound probe 10 at the position that does not constituting an obstacle to operability of various switches not illustrated, being arranged on the input operation key layout 51, nor hamper the visibility of the display screen part 81 of the display unit 80 upon swiveling. In addition, the adapter 400 for mounting accessories is fixed on the main unit in the operating posture A or in the first storage posture B, and the fixing is released and easily removed in the second storage posture C.

As discussed so far, with reference to figures from FIG. 1 to FIG. 7, the structure and functions of the portable ultrasound system according to the present embodiment have been explained, and its main features and effects are as the following.

The first feature of the portable ultrasound system according to the present embodiment is that the keyboard unit 50 and the display unit 80 are independently supported rotatably on the main body unit 30. With this feature, it is possible to achieve various postures as the following; the operating posture in which the main body unit 30 and the keyboard unit 50 are set to be substantially horizontal, and only the display unit 80 is made to stand up, the first storage posture in which the keyboard unit 50 and the display unit 80 are made to stand up with respect to the main body unit 30, and the second storage posture in which the keyboard unit 50 and the display unit 80 are set to be parallel with respect to the main body unit 30. Advantages of this embodiment are obvious relative to a conventional note-type or vertical-type portable ultrasound system. In other words, in a conventional portable ultrasound system, it is possible to take the operating posture, but in the note-type system, only the display unit is movable. Therefore, a storage posture being flat with respect to the installation area (the second storage posture) may be taken, but a wide installation area is necessary. On the other hand, a vertical-type system has a structure to fold the keyboard unit, it is possible to take the storage posture with less installation area (the first posture), but it is unavoidable to take the storage posture being voluminous, rising up massively on the installation surface. According to the present embodiment, it is possible to take various storage postures in response to the installation area and volume.

The second feature of the present embodiment is that the rotation axis P1 of the first rotation axis part 100 for rotating the keyboard unit 50, and the rotation axis P2 of the second rotation axis part 200 for rotating the display unit 80 are placed on the same axis P, under the condition that the display unit 80 takes a basic posture (no swiveling state). With this feature, in the state where the relation between the keyboard unit 50 and the display unit 80 is fixed, for example, both are locked, they are allowed to simultaneously rotate with respect to the main body unit 30. In other words, if the rotation axis P1 and the rotation axis P2 are parallel to each other and placed on different axes, respectively, and the keyboard unit 50 and the display unit 80 are rotated respectively with respect to the main body unit, displacement occurs therebetween, and this may cause a scratch because they come into contact with each other. In the case where the lock mechanism is provided, it is necessary to provide separate lock mechanisms respectively for the first storage posture as shown in FIG. 1(*b*) and for the second storage posture as shown in FIG. 1(*c*). On the other hand, in the present embodiment, the rotation axis P1 and the rotation axis P2 are provided on the same axis, such problem as described above may not occur, and it is possible to achieve locking between the keyboard unit 50 and the display unit 80, and this locking allows protection of the display screen, and the like.

The third and fourth features of the portable ultrasound system according to the present embodiment are as the following; the second rotation axis part 200 for rotating the display unit 80 is configured as also rotatable with respect to the axis Q being perpendicular to the rotation axis P1, and the plane for swiveling of the second rotation axis part 200 is provided on the main body side, relative to the rotation axis P1. In other words, in the present embodiment, the movable axis part of the second rotation axis part 200 is coupled to the main body unit via the rotation axis Q. With those features above, even though the structure of the second rotation axis part 200 is strengthened, it is possible to achieve rotation about the rotation axis P1 and rotation about the axis Q, in the structure being compact without degrading the design.

The fifth feature of the portable ultrasound system according to the present embodiment is that the bent part is formed on the keyboard unit 50, and the first rotation axis part is provided on the bent part. With this feature, in the first storage posture and the second storage posture in which the keyboard unit 50 and the display unit 80 are joined, it is possible to maintain the primary plane of the keyboard unit 50 to be substantially parallel to the primary plane of the display unit 80, achieving a device structurally stable against external forces and actions, and allowing a publicly known lock mechanism to be installed between the keyboard unit and the display unit.

The sixth feature of the portable ultrasound system according to the present embodiment is that the shape of the front surface of the main body unit 30 is formed in such a manner as meeting the demands in shapes and structures of the first rotation axis part 100 and the second rotation axis part 200. For example, by forming the shape of the front surface to be inclined rearward from the lower end toward the upper end, thereby allowing compact installation of the rotation axis part 100 having a robust structure. The shape of the front surface is an arc-like shape extending from both edges toward the center, thereby providing a wide plane R for swiveling to the second rotation axis part 200, strengthening the support structure for swiveling, and enabling a stable swiveling operation. The rearward inclination angle θ2 of both edges of the main body front surface is made to coincide with the inclination angle θ1 of the bent part 55 of the keyboard unit 50 constituting the first rotation axis part 100, whereby it is possible to enhance the design of the front surface of the main body unit 30 in the first storage posture, without enlarging the depth of the input operation key layout 51 on the keyboard unit 50.

Other features and effects produced therefrom of the portable ultrasound system according to the present embodiment, are clarified by the drawings, and the explanations in association therewith.

The portable ultrasound system of the present invention is not limited to the aforementioned embodiment, but various modifications are possible.

By way of example, in the figures, an example is illustrated that the first rotation axis part 100 is made up of a pair of the fixed axis parts and the arm parts placed on both ends of the fixed axis part, but the number of arm parts and their arrangements are not limited to those as illustrated. It is further possible to configure such that three arm parts support one fixed axis part. In addition, an example has been illustrated that the second rotation axis part 200 is placed at the center of the main body unit 30. However, it is alternatively possible to configure such that the second rotation axis part is positioned, being displaced from the center of the main body unit 30, and the first rotation axis parts 100 are arranged on both sides thereof or it may be arranged on one side thereof.

Each size (height, depth, and width) being indicated as to the main body unit 30, the keyboard unit 50, and the display unit 80 is just an example, and the size, and the like, may be modified, as far as the structure and functions being the features of the portable ultrasound system of the present invention are not degraded.

INDUSTRIAL APPLICABILITY

According to the present invention, it is possible to provide a portable ultrasound system superior in operability, storage properties, and design.

EXPLANATION OF REFERENCES

1 . . . portable ultrasound system, 10 . . . ultrasound probe, 11 . . . ultrasound transmitter and receiver, 12 . . . probe connector, 13 . . . DSC, 14 . . . memory part, 15 . . . display device, 16 . . . input device, 17 . . . controller, 18 . . . auxiliary device, 19 . . . power unit, 30 . . . main body unit, 31 . . . rotation axis base part, 32 . . . extended part, 33 . . . bearing part, 50 . . . keyboard unit, 51 . . . input operation key layout, 52 . . . the first arm part, 53 . . . notch, 54 . . . handle part, 55 . . . bent part, 56 . . . indentation, 57 . . . notch, 80 . . . display unit, 81 . . . display screen part, 82 . . . the second arm part, 83 . . . display part installation surface, 100 . . . the first rotation axis part, 101 . . . fixed axis part, 200 . . . the second rotation axis part, 201 . . . movable axis part, 202 . . . bearing part, 203 . . . rim, 204 . . . rearward rim, 205 . . . fitting hole, 251 . . . swiveling axis, 252 . . . movable contact surface, 253 . . . fixed contact surface, 300 . . . unit lock mechanism, 301 . . . hook, 302 . . . opening for locking, 303 . . . release button, 400 . . . adapter for mounting accessories, 401 . . . installation leg, 402 . . . projection, 410 . . . primary supporter, 411 . . . lateral supporter, 412 . . . reinforcing supporter, 420 . . . table top, 421 . . . aperture, 422 . . . notch, 423 . . . aperture cover, 450 . . . mount

What is claimed is:

1. A portable ultrasound system comprising,
a main body unit incorporating an ultrasound measuring part, a display unit coupled to the main body unit, having a display part for displaying an image generated by the ultrasound measuring part, and a keyboard unit coupled to the main body unit, having an input device for inputting information necessary for the ultrasound measuring part,
wherein a front surface of the main body unit has a shape inclining rearward from a lower surface of the main body unit to an upper surface of the main body unit, and
the portable ultrasound system further comprising,
a first rotation axis part for axially supporting the keyboard unit in rotatable manner about a first axis with respect to the main body unit,
a second rotation axis part for axially supporting the display unit in rotatable manner about a second axis with respect to the main body unit; wherein the second rotation axis part includes:
an arm part formed on the lower end of the display unit;
a movable axis part coupled to the arm part, wherein the arm part is axially supported in rotatable manner about the second axis on the movable axis part; and
a rotation axis base part formed on the front surface of the main body unit and serving as a bearing of the movable axis part, wherein the rotation axis base part is formed on a protrusion of the front surface of the main body unit extending in arc-like manner toward the front surface in the depth direction, and
a bearing part for supporting the second rotation axis part in rotatable manner about a third axis being perpendicular to the second axis, wherein the movable axis part is supported rotatably about the third axis on the bearing part,
wherein the first axis and the second axis are on the same axis but independently provided, and the display unit and the keyboard unit are capable of rotating with respect to the main body unit independently.

2. The portable ultrasound system according to claim 1, wherein,
the keyboard unit has a placement surface where the input device is arranged, and a bent part that is bent with respect to the placement surface, and on the bent part, an arm part constituting the first rotation axis part is formed.

3. The portable ultrasound system according to claim 2, wherein,
the first rotation axis part comprises a fixed axis part being fixed on the main body unit, and a pair of the arm parts respectively arranged on both ends of the fixed axis part, and the bent part has a notch for placing the fixed axis part between the pair of the arm parts.

4. The portable ultrasound system according to claim 2, wherein,
the bent part formed on the keyboard unit has a notch for placing the second rotation axis part.

5. The portable ultrasound system according to claim 1, wherein,
the movable axis part has a concave part for supporting the arm part of the display unit, and axially supports the arm part in the concave part.

6. The portable ultrasound system according to claim 5, wherein,
the concave part of the movable axis part has a member mounting part, for mounting a different member, in a portion other than a range for movement of the arm part.

7. The portable ultrasound system according to claim 6, wherein,
the different member is an adapter for placing a probe.

8. The portable ultrasound system according to claim 5, wherein,
the main body unit has a shape of substantially rectangular solid, and when a size of the main body unit is defined by height, width, and depth, the depth is smaller than the width.

9. The portable ultrasound system according to claim 8, wherein,
the keyboard unit and the display unit are connected to the front surface of the main body unit, the width of each unit is substantially equal to the width of the main body unit, and the depth of the main body unit is smaller than the depth of the keyboard unit and the depth of the display unit.

10. The portable ultrasound system according to claim 5, wherein,
the keyboard has an indentation which is provided to avoid interference with the protrusion on the front surface of the main body unit, when the display unit rotates about the first axis.

11. The portable ultrasound system according to claim 5, further comprising a lock mechanism for locking the keyboard unit and the display unit in a first storage posture.

12. The portable ultrasound system according to either of claim 5 and claim 11, further comprising a lock mechanism for locking the keyboard unit and the display unit in a second storage posture in such a manner that the keyboard unit and the display unit are substantially parallel to the main body unit.

* * * * *